United States Patent [19]

Binder et al.

[11] 4,175,085
[45] Nov. 20, 1979

[54] THIENOTHIAZINE DERIVATIVES

[75] Inventors: Dieter Binder; Otto Hromatka, both of Vienna, Austria; Rudolf Pfister, Basel; Paul Zeller, Allschwil, both of Switzerland

[73] Assignee: Hoffmann-La Roche Inc., Nutley, N.J.

[21] Appl. No.: 882,723

[22] Filed: Mar. 2, 1978

Related U.S. Application Data

[62] Division of Ser. No. 767,016, Feb. 9, 1977, Pat. No. 4,090,070.

[30] Foreign Application Priority Data

Feb. 23, 1976 [AT] Austria .................................. 1268/76
Jan. 5, 1977 [CH] Switzerland ............................. 83/77

[51] Int. Cl.$^2$ ...................... C07D 333/24; A01N 9/00
[52] U.S. Cl. ...................................... 549/65; 424/27 S
[58] Field of Search ................................ 260/332.2 A

[56] References Cited

PUBLICATIONS

Chemical Abstracts (1976), vol. 85:5612r.

*Primary Examiner*—A. Siegel
*Attorney, Agent, or Firm*—Jon S. Saxe; George M. Gould; Peter R. Shearer

[57] ABSTRACT

Thienothiazine derivatives of the formula

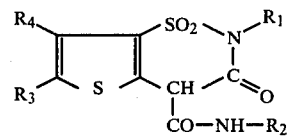

I wherein $R_1$ is lower alkyl; $R_2$ is an unsubstituted aromatic heterocyclic radical which contains from 1 to 4 hetero atoms or one which is substituted by one or two lower alkyl groups, or is an unsubstituted phenyl radical or one substituted by halogen, hydroxy, lower alkyl, nitro, trifluoromethyl or lower alkoxy; and $R_3$ and $R_4$, independently, are hydrogen or lower alkyl, prepared inter alia, from novel intermediates, are described. The end products are useful as anti-inflammatory, analgesic and anti-rheumatic agents.

6 Claims, No Drawings

THIENOTHIAZINE DERIVATIVES

This is a division, of application Ser. No. 767,016, filed Feb. 9, 1977, now U.S. Pat. No. 4,090,020, issued May 16, 1978.

BRIEF SUMMARY OF THE INVENTION

The thienothiazine derivatives of the invention are compounds of the formula

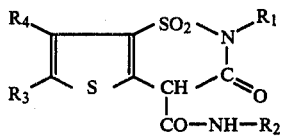

wherein $R_1$ is lower alkyl; $R_2$ is an unsubstituted aromatic heterocyclic radical which contains from 1 to 4 hetero atoms or one which is substituted by one or two lower alkyl groups, or is an unsubstituted phenyl radical or one substituted by halogen, hydroxy, lower alkyl, nitro, trifluoromethyl or lower alkoxy; and $R_3$ and $R_4$, independently, are hydrogen or lower alkyl, and pharmaceutically acceptable salts thereof. The end products are useful as anti-inflammatory, analgesic and anti-rheumatic agents.

In another aspect, the invention relates to intermediates of the formulas

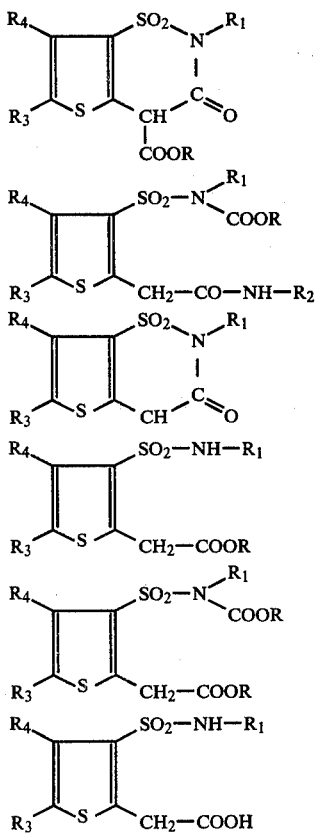

wherein R is lower alkyl and $R_1$, $R_2$, $R_3$ and $R_4$ are as hereinbefore described.

DETAILED DESCRIPTION OF THE INVENTION

The invention relates to compounds of the formula

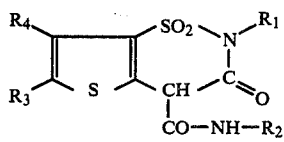

wherein $R_1$ is lower alkyl; $R_2$ is an unsubstituted aromatic heterocyclic radical which contains from 1 to 4 hetero atoms or one which is substituted by one or two alkyl groups, or is an unsubstituted phenyl radical or one substituted by halogen, hydroxy, lower alkyl, nitro, trifluoromethyl or lower alkoxy; and $R_3$ and $R_4$, independently, are hydrogen or lower alkyl, and pharmaceutically acceptable salts thereof.

The compounds of formula I can also exist in the tautomeric form of the formula

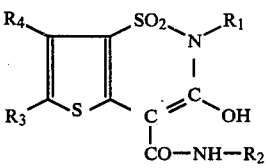

wherein $R_1$, $R_2$, $R_3$ and $R_4$ are as hereinbefore described.

The term "lower alkyl" as used herein denotes a straight-chain or branched-chain saturated hydrocarbon of 1 to 4 carbon atoms, for example, methyl, ethyl, propyl, isopropyl, t-butyl, or the like. The term "lower alkoxy" denotes an alkyl ether group in which the lower alkyl group is as described above, for example, methoxy, ethoxy, propoxy, pentoxy, or the like. The term "halogen" denotes all the halogens, i.e., chlorine, bromine, fluorine and iodine. The term "unsubstituted aromatic heterocyclic radical which contains 1 to 4 hetero atoms, or one which is substituted by one or two lower alkyl groups" denotes a 5-membered or 6-membered aromatic heterocyclic radical which contains up to 4 nitrogen and/or oxygen and/or sulfur atoms and which is optionally substituted by one or two lower alkyl groups, for example, 2-thiazolyl, 4-methyl-2-thiazolyl, 4,5-dimethyl-2-thiazolyl, 5-methyl-1,3,4-thiadiazolyl, 2-pyrazinyl, 2-pyrimidinyl, 1,2,4-triazin-3-yl, 2-pyridyl, 3-pyridyl, 4-pyridyl, 3-methyl-2-pyridyl, 4-methyl-2-pyridyl, 5-methyl-2-pyridyl, 6-methyl-2-pyridyl, 4,6-dimethyl-2-pyridyl, 5-isoxazolyl, 5-methyl-3-isoxazolyl, 3,4-dimethyl-5-isoxazolyl, 2,6-dimethyl-4-pyrimidinyl, 1,2,3,4-tetrazol-5-yl, or the like.

Preferred compounds of formula I are those wherein $R_3$ and $R_4$ each is hydrogen. $R_1$ preferably is methyl and $R_2$ preferably is 2-thiazolyl, 5-methyl-3-isoxazolyl or 2-pyridyl. Other preferred definitions of $R_2$ are 4-fluorophenyl, 3-trifluoromethylphenyl, 2,4-dichlorophenyl, 4-bromophenyl, 4-chlorophenyl, 4-nitrophenyl, 3-chlorophenyl, 2-tolyl, 2,5-dichlorophenyl, 4-nitro-2-tolyl, 4-iodophenyl and 4-n-butylphenyl.

Preferred compounds of formula I are 3,4-dihydro-2-methyl-3-oxo-4-(2-pyridylcarbamoyl)-2H-thieno[2,3-e]1,2-thiazine 1,1-dioxide and 3,4-dihydro-2-methyl-3- oxo-4-(2-thizolyl-carbamoyl)-2H-thieno[2,3-e] 1,2-thiazine 1,1-dioxide.

The aforementioned thienothiazine derivatives, that is, the compounds of formula I and their salts, are prepared by (a) reacting a compound of the formula

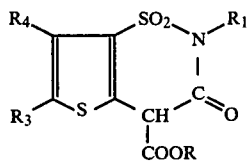   II wherein R is lower alkyl and $R_1$, $R_3$ and $R_4$ are as hereinbefore described,
with an amine of the formula

   III wherein $R_2$ is as hereinbefore described,
or
(b) cyclizing a reactive acid derivative of the formula

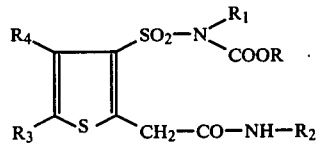   IV wherein R, $R_1$, $R_2$, $R_3$ and $R_4$ are as hereinbefore described,
or
(c) reacting a compound of the formula

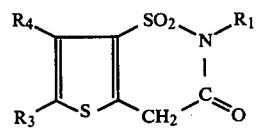   V wherein $R_1$, $R_3$ and $R_4$ are as hereinbefore described, with an isocyanate of the formula

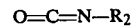   VI wherein $R_2$ is as hereinbefore described, in the presence of a strong base, and (d) if desired, converting a resulting compound of formula I into a pharmaceutically acceptable salt.

The reaction of a compound of formula II with an amine of formula III according to process embodiment (a) can optionally be carried out in the presence of an inert solvent. Suitable solvents are alcohols, for example, ethanol, or the like; hydrocarbons, for example, benzene, toluene, xylene, or the like; halogenated hydrocarbons, for example, chloroform, chlorobenzene, methylene chloride, carbon tetrachloride, or the like; or dimethylformamide or dioxane. The reaction is preferably carried out by warming the mixture, preferably to the melting point or reflux temperature of the reaction mixture.

According to process embodiment (b), a reactive acid derivative of formula IV is cyclized. The cyclization is carried out in the presence of a base, and preferably in the presence of a solvent, at a temperature in the range of from about 0° C. to about the reflux temperature of the mixture, preferably in the range of from room temperature to 60° C. Suitable bases are, in particular, hydrides, amides and alcoholates of alkali metals. Suitable solvents are aprotic and protic solvents, for example, alcohols such as methanol, ethanol; ethers, such as dioxane; acid amides, such as dimethylformamide; dimethylsulfoxide, or the like. The cyclization is appropriately carried out by dissolving the reactive acid derivative of formula IV in the solvent, adding the base and either allowing the mixture to stand at room temperature for 1 to 4 hours or warming it to a temperature of up to 60° C. Suitable reactive acid derivatives of formula IV are, in particular, the methyl esters.

According to process embodiment (c), a compound of formula V is reacted with an isocyanate of formula VI in the presence of a strong base. Suitable strong bases are, above all, tertiary amines, and in particular trialkylamines, such as, triethylamine. The reaction is preferably carried out under an atmosphere of gas, for example, under nitrogen, at a temperature in the range of from about 0° C. to about 50° C., preferably at room temperature, and in the presence of an aprotic solvent, for example, toluene, dioxane, dimethylformamide, dimethylsulfoxide or hexamethylphosphoric acid triamide (HMTP). The isocyanates of formula VI required as the starting materials are either known or can be synthesized in a manner analogous to that used for the known starting materials.

The starting materials of formulas, II, IV and V can be prepared according to the following reaction sequence, wherein Hal is halogen and R, $R_1$, $R_2$, $R_3$ and $R_4$ are as hereinbefore described.

Reaction Sequence

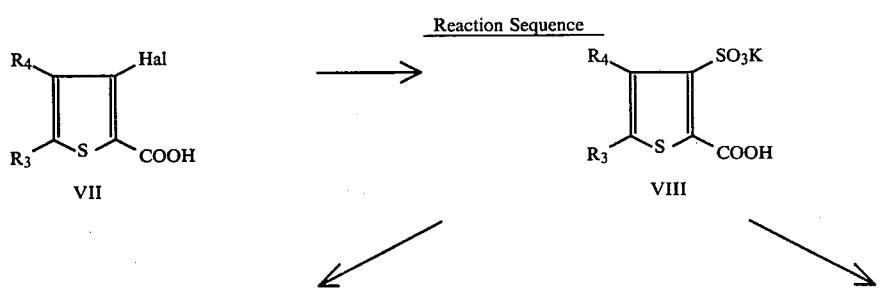

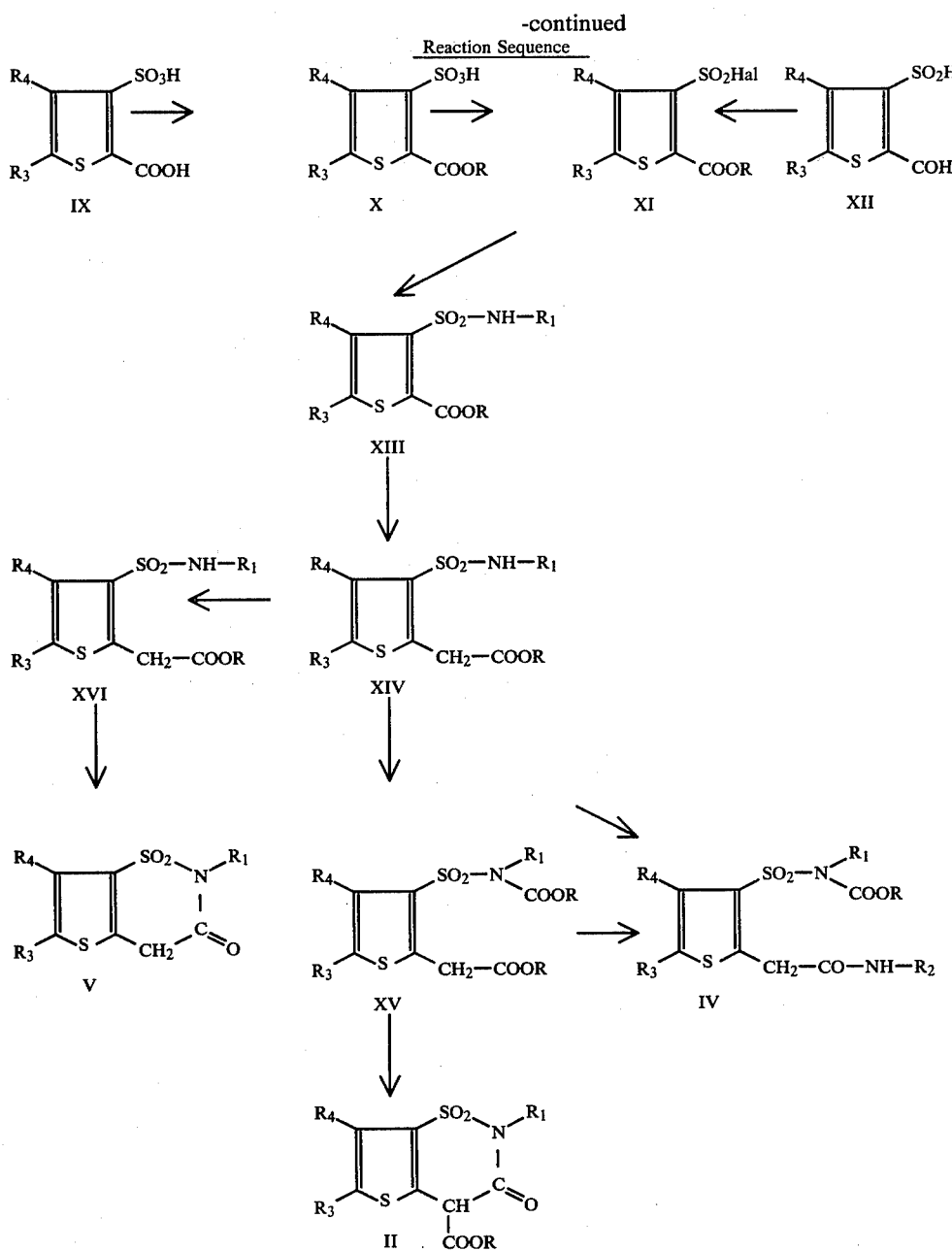

A known compound of formula VII is 3-chloro-thiophene-2-carboxylic acid, which has been prepared by a method described in the art. A new method for the preparation of 3-chloro-thiophene-2-carboxylic acid consists in intermediately converting 3-hydroxythiophene-2-carboxylic acid methyl ester, which is known, into 3-chlorothiophene-2-carboxylic acid chloride in an inert solvent which boils above 80° C., for example, chloroform or dioxane, using a chlorinating agent, for example, phosphorus pentachloride, and hydrolyzing the chloride compound to give the corresponding acid. Substituted 3-chloro-thiophene-2-carboxylic acids, that is, compounds of formula VII wherein Hal is chlorine and $R_3$ and/or $R_4$ are other than hydrogen can be prepared analogously. Although in principle a bromine compound can be used as the starting material for the preparation of a compound of formula VIII described hereinafter, it is advisable to use the corresponding chlorine compound.

The conversion of a compound of formula VII into a compound of formula VIII is carried out, using known methods, by reacting the compound of formula VII with sodium hydrogen sulfite in the presence of a copper-(I) salt catalyst, in particular copper-(I) chloride, and reacting the resulting product with potassium chloride. During the reaction with sodium hydrogen sulfite a temperature of 143° C. should be maintained in order to achieve optimum yields.

The conversion of a compound of formula VIII into the compound of formula IX is carried out in a known manner, for example, by means of a strong ion exchanger.

The esterification of a compound of formula IX to a compound of formula X is carried out autocatalytically, due to the presence of the sulfo group, in an alcohol/- chloroform mixture. A methyl ester is obtained by dissolving a compound of formula X in the methanol/chloroform and heating the mixture to the boiling point of the ternary azeotrope, that is, methanol/chloroform/water, of the reaction mixture.

The halogenation of a compound of formula X into a compound of formula XI is carried out in a known manner using a halogenating agent, preferably a chlorinating agent, for example, thionyl chloride or phosphorus pentachloride. Chlorination with thionyl chloride can be carried out without a solvent by heating the mixture to reflux. If phosphorus pentachloride is used, the chlorination can be carried out in the presence of an inert solvent, for example, chloroform, carbon tetrachloride or dioxane, at a temperature in the range of from about 50° C. to about the reflux temperature of the mixture.

However, a compound of formula XI can also be prepared from a compound of formula VIII via a compound of formula XII. The compound of formula VIII is reacted, for example, with 2 moles of phosphorus pentachloride in the presence of phosphorus oxychloride, as the solvent, at a temperature in the range of from about 30° C. to about the boiling point of phosphorus oxychloride. An inert organic solvent, for example, dioxane, chloroform, carbon tetrachloride, benzene, toluene or the like, can be used in place of phosphorus oxychloride. The esterification of a compound of formula XII to a compound of formula XI is carried out utilizing the corresponding alcohol, in particular methanol, at a temperature in the range of from about room temperature to about the reflux temperature. The solvent can be the alcohol or an inert solvent, such as chloroform, carbon tetrachloride, dioxane or benzene.

A compound of formula XI is then aminoalkylated to a compound of formula XIII in a known manner by reacting it with an alkylamine of the formula $R_1$—$NH_2$  XVII wherein $R_1$ is as hereinbefore described,
in the presence of an inert organic solvent, for example, chloroform, methylene chloride, carbon tetrachloride, benzene or dioxane at room temperature.

A compound of formula XIII is then saponified to a corresponding free carboxylic acid, for example, by heating with alkali, for example, potassium hydroxide, preferably in an aqueous/alcoholic medium. The resulting free carboxylic acid is then converted into a corresponding acid chloride, which is then converted into a corresponding diazomethyl ketone using diazomethane. The latter yields a corresponding compound of formula XIV on treatment with silver nitrate and a lower alkanol. The product is obtained in two isomeric conformations, one of which corresponds to formula XIV. The other, as a result of a chelate-like hydrogen bridge, has a cyclic structure. Corresponding compounds of formula XVI and/or V may also be formed as by-products. Reaction of a compound of formula XIV or its conformation isomers with a chloroformic acid ester of the formula Cl—CO—OR  XVIII wherein R is as hereinbefore described,
in the presence of a strong base, for example, sodium methylate, gives a compound of formula XV. The compound of formula XV can be converted into a corresponding compound of formula II by a cyclization analogous to the cyclization reaction described hereinbefore for a compound of formula IV, for example, by warming with sodium hydride in dioxane.

A compound of formula IV is prepared by reacting a compound of formula XIV, a conformation isomer thereof, or a compound of formula XV with an amine of formula III in a manner analogous to that described hereinbefore for compounds of formulas II and III. If a compound of formula XIV is utilized, the resulting product is subsequently reacted with a compound of formula XVIII in the presence of a strong base.

A compound of formula V can be prepared by saponifying a compound of formula XIV or a conformation isomer thereof, for example, under alkaline conditions, and subsequently cyclizing the resulting compound of formula XVI, for example, by treatment with thionyl chloride.

The compounds of formulas II, IV, V and XIV to XVI are novel and comprise another aspect of the present invention, as do the processes for the preparation of said compounds.

The compounds of formula I can form salts with pharmaceutically acceptable bases. Suitable bases are those of the alkali metals, for example lithium, sodium, potassium and the alkaline earth metals, for example, magnesium and calcium, and amines, such as triethanolamine, diethylaminoethanol, triethylamine, trimethylamine, diethylamine or the like. The compounds of formula I wherein $R_2$ is a basic heterocyclic radical, can also form pharmaceutically acceptable acid addition salts with strong acids, in particular with mineral acids, for example, hydrochloric acid.

The compounds of formula I and their pharmaceutically acceptable salts have an anti-inflammatory, analgesic and anti-reheumatic activity, and are therefore useful as anti-inflammatory, analgesic and anti-rheumatic agents. The valuable pharmacological properties of the compounds of formula I can be determined utilizing standard methods, for example, in the known kaolin paw inflammation test (on rats). In this test, an acute local inflammation is produced in the right hind paw of the rat by intradermal injection of 0.1 ml. of a 10% strength kaolin suspension (bolus alba). The substance to be investigated is administered orally and the following parameters are measured:

1. Diameter of the paw in mm—as an expression of the severity of the inflammation;
2. Pressure, in g, on the paw—to determine the pain threshold.

The substance to be tested is administered half an hour before and three and a half hours after the kaolin injection and the parameters mentioned hereinbefore are measured 4 hours after the kaolin injection. The inhibiting effect on the inflammation is given in percentages, based on the difference in the intensity of inflammation between untreated animals and animals treated with the substance to be investigated. The antinosiceptive activity is given by the percentage increase in the pain threshold.

In these tests the compound of formula I, wherein $R_1$ is methyl, $R_2$ is p-bromophenyl and $R_3$ and $R_4$ are hydrogen shows at a dosage of 10 mg/kg p.o. a 25% inhibition of the edema and a 51% increase of the pain threshold.

In this test, compounds of formula I and their pharmaceutically acceptable salts show an inhibition of inflammation and an increase in the pain threshold. In addition, they inhibit—as can be shown in a corresponding standard test—the blood platelet aggregation and, accordingly, also have antithrombotic properties.

Qualitatively, the compounds of formula I and their pharmaceutically acceptable salts have a similar action to phenylbutazone, which is known for its therapeutic use and properties.

The compounds of formula I and their pharmaceutically acceptable salts can be used as medicaments, for example, in the form of pharmaceutical preparations which contain them in association with a compatible pharmaceutical carrier material. Such carrier material can be an organic or inorganic inert material which is suitable for enteral or parenteral application, for example, water, gelatin, gum arabic, lactose, starch, magnesium stearate, talc, vegetable oils, polyalkylene glycols, or the like. The pharmaceutical preparations can be made up in a solid form, for example, as tablets, dragees, suppositories or capsules, in a semi-solid form, for example, as ointments, or in a liquid form, for example, as solutions, suspensions or emulsions. The pharmaceutical preparations may be sterilized and/or may contain compatible adjuvants, such as, preservatives, stabilizing agents, emulsifying agents, salts for modifying the osmotic pressure or buffering agents. They can also contain other therapeutic substances.

The Examples which follow further illustrate the invention. All temperatures are in degrees Centigrade, unless otherwise mentioned.

EXAMPLE 1

3,4-Dihydro-2-methyl-3-oxo-4-(2-pyridyl-carbamoyl)-2H-thieno[2,3-e]1,2-thiazin 1,1-dioxide 52.1 G. of phosphorus pentachloride are dissolved in 600 ml. of absolute carbon tetrachloride. After the solution is heated to the boiling point, a solution of 15.8 g. of 3-hydroxy-2-methoxycarbonyl-thiophene in 200 ml. of carbon tetrachloride is added dropwise over a period of 3 hours. Then, the mixture is boiled under reflux for 13 hours. Thereafter, the carbon tetrachloride is removed by distillation and the reaction mixture is evaporated almost to dryness in vacuo. There are then added 450 ml. of water dropwise, while cooling, and the mixture is heated to the boiling point and allowed to cool. The precipitated product is removed by distillation and boiled up in a solution of 25 g. of sodium bicarbonate with 10 g. of activated charcoal. The activated charcoal is then removed by filtration. The cooled solution is acidified with hydrochloric acid and 3-chloro-thiophene-2-carboxylic acid, melting point 185° C. to 186° C. is obtained.

8.6 G. of 3-chlorothiophene-2-carboxylic acid are dissolved in 23 ml. of water, containing 2.1 g. of sodium hydroxide, in a glass autoclave. Thereafter, a solution of 5.6 g. of sodium bisulfite in 16 ml. of water is added and the solution is rendered just alkaline with 30% strength sodium hydroxide solution. Then, 0.43 g. of copper-(I) chloride is added and the mixture is heated to 143° C. for 16 hours. After cooling, the red copper oxide is removed by filtration. The filtrate is acidified with 7 ml. of concentrated hydrochloric acid, during which the unreacted starting material precipitates and is removed by shaking out with methylene chloride. Subsequently, 12 g. of potassium chloride are added to the acid solution, while warming. After cooling to 0° C., the monopotassium salt of 3-sulfo-thiophene-2-carboxylic acid separates out in the form of colorless crystals.

8.2 G. of the potassium salt of 3-sulfo-thiophene-2-carboxylic acid obtained as described hereinbefore are dissolved in 50 ml. of water. The resulting solution is allowed to flow through an ion exchange column which is charged with protons and the column is rinsed with water until the pH value of the outflowing solution is 5. The solution is evaporated to dryness in vacuo and the crystalline residue, which consists of 3-sulfo-thiophene-2-carboxylic acid, is recrystallized from a little water.

7.6 G. of 3-sulfo-thiophene-2-carboxylic acid are dissolved in 140 ml. of absolute methanol and 65 ml. of absolute chloroform, and the solution is boiled under reflux. The water formed during the reaction is removed by distillation as a ternary azeotrope (chloroform/methanol/water) via a packed column (1m). The mixture is then evaporated in vacuo, and 100 ml. of chloroform are added to the residue to remove traces of methanol. Then, the mixture is again evaporated under normal pressure. The residual brown oil, which consists of 3-sulfo-thiophene-2-carboxylic acid methyl ester, crystallizes out immediately after cooling. However, the crystals are hygroscopic and deliquesce in air.

7.4 G. of crude 3-sulfo-thiophene-2-carboxylic acid methyl ester are dissolved in 50 ml. of thionyl chloride and the solution is boiled under reflux for 16 hours. The mixture is evaporated to dryness in vacuo, after which the residual pale yellow oil, which consists of 3-chlorosulfonyl-thiophene-2-carboxylic acid methyl ester, is crystallized by means of petroleum ether.

The conversion of the monopotassium salt of sulfo-thiophene-2-carboxylic acid into 3-chloro-sulfonyl-thiophene-2-carboxylic acid methyl ester can also be carried out as follows:

50 G. of the monopotassium salt of 3-sulfo-thiophene-2-carboxylic acid are suspended in 250 ml. of phosphorus oxychloride and 85 g. of phosphorus pentachloride are added, while stirring. Vigorous evolution of HCl occurs. The mixture is then heated on a water bath for an additional 90 minutes, with stirring, cooled to room temperature and the inorganic salts are removed by filtration. As much phosphorus oxychloride as possible is removed by distillation in vacuo. The oily residue is dissolved in 400 ml. of dry chloroform to remove any inorganic salts still present and the mixture is then filtered and evaporated. The oily residue, which consists of 3-chlorosulfonyl-thiophene-2-carboxylic acid chloride, crystallizes out on cooling and is used in the next step without additional purification.

48 G. of the 3-chlorosulfonyl-thiophene-2-carboxylic acid chlorine obtained as described hereinbefore are dissolved in 500 ml. of absolute chloroform, 9.6 g. of absolute methanol are added, and the mixture is heated under reflux for 3 hours, that is, until evolution of hydrochloric acid has ended. The mixture is then evaporated to dryness in vacuo and the residue, which consists of pure 3-chlorosulfonyl-thiophene-2-carboxylic acid methyl ester, crystallizes out. The crude product can be used in the next step.

43.5 G. of the 3-chlorosulfonyl-thiophene-2-carboxylic acid methyl ester obtained as described hereinbefore are dissolved in 450 ml. of absolute chloroform and dry methylamine is passed into the solution at 10° C. until a moistened pH paper indicates the solution is alkaline. Then, the solution is allowed to react for an additional 2 hours at room temperature, during which time it should be maintained alkaline. The solution is extracted by shaking with 500 ml. of water and then 500 ml. of 5% strength sodium bicarbonate solution. The aqueous phases are each shaken again once with chloroform and the combined organic phases are dried over sodium sulfate and evaporated. The crystalline residue is digested with ether for purification, and 3-methylsulfamoyl-thiophene-2-carboxylic acid methyl ester, melting point 115° C. to 122° C., is obtained.

23.5 G. of 3-methylsulfamoyl-thiophene-2-carboxylic acid methyl ester are dissolved in 50 ml. of ethanol, while warming, 50 ml. of 3-N potassium hydroxide solution are added and the mixture is heated under reflux for 3 hours. After cooling, it is diluted with water and extracted by shaking with methylene chloride. The aqueous phase is acidified with hydrochloric acid and extracted several times with 50 ml. of ether each time. After drying the mixture over sodium sulfate and removal of the solvent by evaporation, colorless crystals which are pure enough for further reaction are obtained. The resulting 3-methyl-sulfamoyl-thiophene-2-carboxylic acid, melting point 182° C. to 184° C., can be recrystallized from water.

11.06 G. of 3-methylsulfamoyl-thiphene-2-carboxylic acid and 15.8 g. of phosphorus pentachloride are suspended in 150 ml. of absolute chloroform and the suspension stirred for 30 minutes at 40° C. Then, the mixture is carefully evaporated in vacuo to half the volume. Thereafter, the mixture is diluted with 400 ml. of absolute ether and the resulting solution is added dropwise to an ethereal diazomethane solution, prepared from 50 g. of nitrosomethylurea and cooled to $-20°$ C., over a period of 1 hour. After removing the cooling bath, the mixture is allowed to react for an additional one and a half hours and then cooled to $-40°$ C. The diazomethyl 3-methyl-sulfamoyl-thiophen-2-yl ketone, melting point 110° C. to 111° C. (from ethanol), which has separated out is removed by filtration. 3 G. of diazomethyl 3-methylsulfamoyl-thiophen-2-yl ketone are dissolved in 30 ml. of absolute methanol, 50 mg. of silver nitrate are added and the mixture is heated under reflux for 45 minutes. Then, the mixture is evaporated in vacuo. Thereafter, the residue is boiled out several times with ether and the combined ether phases stirred with activated charcoal and filtered. The filtrate contains mainly 3-methyl-sulfamoyl-2-thiophenacetic acid methyl ester, in addition to a little 3-methyl-sulfamoyl-2-thiophenacetic acid and 3,4-dihydro-2-methyl-3-oxo-2H-thieno[2,3-e]1,2-thiazine 1,1-dioxide. 3-Methylsulfamoyl-2-thiophenacetic acid is removed by shaking out the ether solution several times with sodium hydrogen carbonate solution, drying and evaporating. The ring of 3,4-dihydro-2-methyl-3-oxo-2H-thieno[2,3-e]1,2-thiazine 1,1-dioxide is opened by taking up the residue of the evaporation mentioned hereinbefore with 12 ml. of 1-N methanolic sodium methylate solution, allowing the solution to stand at room temperature for 20 minutes, then just acidifying with concentrated hydrochloric acid, and finally evaporating to dryness in vacuo. The evaporation residue is taken up with methylene chloride and water and the organic phase is dried and evaproated. The oily residue consists of about equal parts of two conformation isomeric forms of 3-methyl-sulfamoyl-2-thiophenacetic acid methyl ester and can be used in the next step without further purification.

The two forms can be separated by column chromatography (silica gel, particle size 0.063–0.2 mm; eluant: benzene/glacial acetic acid=4:1): form which is eluted more rapidly: $^1$H-NMR (CDCl$_3$): $\delta=7.2$–$7.4(g_{AB}$, 2H, H-4$_{thiophene}$ and H-5$_{thiophene}$), $\delta=4.8$–5.3 (m, 1H, N—H, D$_2$O exchangeable), $\delta=4.15$ (s, 2H, —CH$_2$—COOCH$_3$), $\delta=3.7$ (s, 3H, O—CH$_3$), $\delta=2.65$ (d, 3H, NH—CH$_3$, J=6 Hz). Form which is eluted more slowly: $^1$H-NMR(CDCl$_3$): $\delta=7.65$ (s, 2H, H-4$_{thiophene}$ and H-5$_{thiophene}$), $\delta=5.80$–6.20 (m, 1H, —N—H, D$_2$O exchangeable), $\delta=4.40$(s, 2H, —CH$_2$—COOCH$_3$), $\delta=3.40$ (s, 3H, O—CH$_3$), $\delta=2.6$ ppm (d, 3H, NH—CH$_3$, J=6 Hz).

Both forms decompose on distillation in a high vacuum.

1.15 G. of crude 3-methylsulfamoyl-2-thiophenacetic acid methyl ester are dissolved in 4.7 ml. of 1-N methanolic sodium methylate solution. The solution is evaporated to dryness in vacuo and the residue is taken up with 10 ml. of absolute dimethylformamide and cooled to 0° C. 0.50 G. of chloroformic acid methyl ester is then added dropwise. After stirring for half an hour at room temperature, the mixture is evaporated in vacuo and the residue is taken up in methylene chloride and water. The organic phase is separated, dried and evaporated. The oily residue, which consists of pure 3-(N-methoxycarbonyl-N-methylsulfamoyl)-2-thiophenacetic acid methyl ester, can be used in the next step without further purification.

$^1$H-NMR-spectrum (CDCl$_3$): $\delta=7.2$–$7.4(g_{AB}$, 2H, H-4$_{thiophene}$ and H-5$_{thiophene}$), $\delta=4.2$ (s, 2H, CH$_2$—COOCH$_3$), $\delta=3.65$ (s, 3H, —N—CO—OCH$_3$), $\delta=3.62$ (s, 3H, CH$_2$—COOCH$_3$), $\delta=3.3$ ppm (s, 3H, —N—CH$_3$).

1.42 G. of crude 3-(N-methoxycarbonyl-N-methylsulfamoyl)-2-thiophenacetic acid methyl ester are dissolved in 10 ml. of absolute dioxane and 0.21 g. of a 55% strength sodium hydride suspension (in mineral oil) is added. Thereafter, 50 mg. of methanol are added and the mixture is stirred for 1 hour at 50° C. to 60° C. Then, the mixture is cooled, acidified with glacial acetic acid and evaporated in vacuo. The residue is taken up in methylene chloride and saturated sodium bicarbonate solution. The organic phase is again shaken out several times with sodium bicarbonate solution. Thereafter, the aqueous phases are combined and acidified with concentrated hydrochloric acid. The precipitate which separates is shaken out with methylene chloride and the organic phase is then dried and evaporated. The residue, which crystallizes immediately, consists of pure 3,4-dihydro-4-methoxycarbonyl-2-methyl-3-oxo-2H-thieno[2,3-e]1,2-thiazine 1,1-dioxide, melting point 124° C. to 126° C. (from ether).

0.3 G. of 3,4-dihydro-4-methoxycarbonyl-2-methyl-3-oxo-2H-thieno[2,3-e]1,2-thiazine 1,1-dioxide and 0.13 g. of 2-aminopyridine are dissolved in 30 ml. of absolute xylene and the solution is heated for 1 hour under reflux. After cooling, the crystals are removed by filtration and recrystallized from glacial acetic acid. 3,4-Dihydro-2-methyl-3-oxo-4-(2-pyridyl-carbamoyl)-2H-thieno[2,3-e]1,2-thiazine 1,1-dioxide, melting point 255° C. to 256° C. (decomposition), is obtained.

EXAMPLE 2

Preparation of 3,4-dihydro-2-methyl-3-oxo-4-(2-thiazolyl-carbamoyl)-2H-thieno[2,3-e]1,2-thiazine 1,1-dioxide 0.15 G. of 3,4-dihydro-4-methoxycarbonyl-2-methyl-3-oxo-2H-thieno[2,3-e]1,2-thiazine 1,1-dioxide and 0.071 g. of 2-aminothiazole are dissolved in 30 ml. of absolute xylene and the solution is heated for half an hour under the reflux. After cooling, the crystals are removed by filtration, recrystallized from glacial acetic acid, and 3,4-dihydro-2-methyl-3-oxo-4-(2-thiazolyl-carbamoyl)-2H-thieno[2,3-e]1,2-thiazine 1,1-dioxide, melting point 236° C. to 238° C. (decomposition), is obtained.

EXAMPLE 3

Preparation of 2-hydroxy-2-methyl-N-pyrazinyl-2H-thieno[2,3-e]1,2-thiazine-4-carboxamide 1,1-dioxide 2-Hydroxy-2-methyl-N-pyrazinyl-2H-thieno[2,3-e]1,2-thiazine-4-carboxamide 1,1-dioxide, melting point 222° C. to 223° C. (decomposition) is prepared from 3,4-dihydro-4-methoxycarbonyl-2-methyl-3-oxo-2H-thieno[2,3-e]1,2-thiazine 1,1-dioxide and aminopyrazine by a procedure analogous to that described in Example 2.

EXAMPLE 4

Preparation of 4'-bromo-3-hydroxy-2-methyl-2H-thieno[2,3-e]1,2-thiazine-4-carboxanilide 1,1-dioxide 3.1 G. of 3,4-dihydro-2-methyl-3-oxo-2H-thieno[2,3-e]1,2-thiazine 1,1-dioxide are dissolved in 31 ml. of absolute dimethylsulfoxide under an atmosphere of nitrogen. 1.44 G. of freshly distilled triethylamine and 2.83 g. of 4-bromophenyl isocyanate are added to the solution and the mixture is then stirred for 24 hours at room temperature. This mixture is then poured into 225 ml. of 3-N hydrochloric acid and the prepcipitate which separates out is filtered on a sinter filter, washed three times with 20 ml. of distilled water each time and dried as much as possible. The precipitate is dissolved in 250 ml. of methylene chloride, dried over sodium sulfate, stirred with activated charcoal and filtered. The organic phase is shaken out four times with 250 ml. of saturated sodium bicarbonate solution each time and the aqueous phase is shaken again each time with a little methylene chloride. The combined aqueous phases are rendered strongly acid with concentrated hydrochloric acid. The product which separates out is extracted three times with 250 ml. of methylene chloride each time. The combined organic phases are dried over sodium sulfate, stirred with activated charcoal, filtered and the solvent is removed by distillation. The crystalline residue is dissolved in 50 ml. of chloroform. While boiling, activated charcoal is added and the mixture is filtered hot. The product is made to crystallize by scratching. The crystals are removed by filtration, digested with a little cold chloroform, and 4'-bromo-3-hydroxy-2-methyl-2H-thieno[2,3-e]1,2-thiazine-4-carboxanilide 1,1-dioxide, melting point 178° C. to 179° C. (decomposition), is obtained.

EXAMPLE 5

Preparation of 4'-chloro-3-hydroxy-2-methyl-2H-thieno[2,3-e]1,2-thiazine-4-carboxanilide 1,1-dioxide 4'-Chloro-3-hydroxy-2-methyl-2H-thieno[2,3-e]1,2-thiazine-4-carboxanilide 1,1-dioxide, melting point 172° C. to 173° C. is prepared by a procedure analogous to that described in Example 4 using 4-chlorophenyl isocyanate.

The following Examples illustrate representative pharmaceutical preparations provided by this invention:

EXAMPLE A

Suppositories of the following composition are produced in a known, customary manner:

| | |
|---|---|
| 3,4-Dihydro-2-methyl-3-oxo-4-(2-pyridyl-carbamoyl)-2H-thieno[2,3-e]1,2-thiazine 1,1-dioxide | 0.025 g. |
| Hydrated coconut oil | 1.230 g. |
| Carnuba wax | 0.045 g. |

EXAMPLE B

Tablets of the following composition are produced in a known, customary manner:

| | Per Tablet |
|---|---|
| 3,4-Dihydro-2-methyl-3-oxo-4-(2-pyridyl-carbamoyl)-2H-thieno[2,3-e]1,2-thiazine 1,1-dioxide | 25.00 mg. |
| Lactose | 64.50 mg. |
| Maize starch | 10.00 mg. |
| Magnesium stearate | 0.50 mg. |

EXAMPLE C

Capsules of the following composition are produced in a known, customary manner:

| | Per Capsule |
|---|---|
| 3,4-Dihydro-2-methyl-3-oxo-4-(2-pyridyl-carbamoyl)-2H-thieno[2,3-e] 1,2-thiazine 1,1-dioxide | 50 mg. |
| Lactose | 125 mg. |
| Maize starch | 30 mg. |
| talc | 5 mg. |
| Total Weight | 210 mg. |

We claim:

1. A compound of the formula

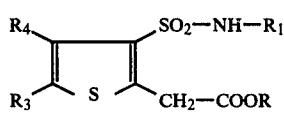

XIV wherein R is lower alkyl, $R_1$ is lower alkyl, and $R_3$ and $R_4$, independently, are hydrogen or lower alkyl.

2. A compound in accordance with claim 1, 3-methylsulfamoyl-2-thiophenacetic acid methyl ester.

3. A compound of the formula

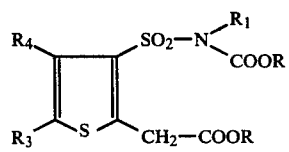

XV wherein R is lower alkyl, $R_1$ is lower alkyl, and $R_3$ and $R_4$, independently, are hydrogen or lower alkyl.

4. A compound in accordance with claim 3, 3-(N-methoxycarbonyl-N-methylsulfamoyl)-2-thienophenacetic acid methyl ester.

5. A compound of the formula

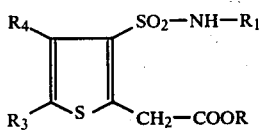 XVI
wherein $R_1$ is lower alkyl, and $R_3$ and $R_4$, independently, are hydrogen or lower alkyl.
6. A compound in accordance with claim 5, 3-methyl-sulfamoyl-2-thiophenacetic acid.
* * * * *
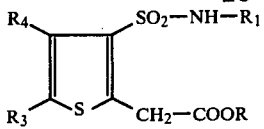 XVI
wherein $R_1$ is lower alkyl, and $R_3$ and $R_4$, independently, are hydrogen or lower alkyl.
6. A compound in accordance with claim 5, 3-methyl-sulfamoyl-2-thiophenacetic acid.
* * * * *